(12) United States Patent
Moffitt et al.

(10) Patent No.: US 8,494,626 B2
(45) Date of Patent: Jul. 23, 2013

(54) IMPLANTABLE NEUROSTIMULATORS HAVING REDUCED POCKET STIMULATION

(75) Inventors: Michael A. Moffitt, Valencia, CA (US); Dongchul Lee, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 162 days.

(21) Appl. No.: 12/630,591

(22) Filed: Dec. 3, 2009

(65) Prior Publication Data

US 2010/0137961 A1 Jun. 3, 2010

Related U.S. Application Data

(62) Division of application No. 12/629,814, filed on Dec. 2, 2009.

(60) Provisional application No. 61/119,662, filed on Dec. 3, 2008.

(51) Int. Cl.
*A61N 1/00* (2006.01)

(52) U.S. Cl.
USPC ...... 607/2; 607/39; 607/41; 607/46; 607/116; 607/118

(58) Field of Classification Search
USPC .................. 607/2, 39, 41, 46, 116, 118
See application file for complete search history.

(56) References Cited

U.S. PATENT DOCUMENTS

| | | | |
|---|---|---|---|
| 5,354,296 A | 10/1994 | Turkel | |
| 6,393,325 B1 * | 5/2002 | Mann et al. | 607/46 |
| 6,582,441 B1 | 6/2003 | He et al. | |
| 6,793,048 B1 | 9/2004 | Groves et al. | |
| 6,941,171 B2 | 9/2005 | Mann et al. | |
| 7,389,140 B1 | 6/2008 | Kroll | |
| 2002/0193859 A1 | 12/2002 | Schulman et al. | |
| 2003/0114905 A1 | 6/2003 | Kuzma | |
| 2004/0059392 A1 | 3/2004 | Parramon et al. | |
| 2004/0162590 A1 | 8/2004 | Whitehurst et al. | |

(Continued)

FOREIGN PATENT DOCUMENTS

| | | |
|---|---|---|
| WO | WO 98/37926 A1 | 9/1998 |
| WO | WO 98/43700 A1 | 10/1998 |
| WO | WO 98/43701 A1 | 10/1998 |
| WO | WO 2007/059343 A2 | 5/2007 |

OTHER PUBLICATIONS

Wiley, J.D., et al., Analysis and Control of the Current Distribution under Circular Dispersive Electrodes, IEEE TBME, vol. BME-29, No. 5, May 1982, 381-385.

(Continued)

*Primary Examiner* — Christopher D Koharski
*Assistant Examiner* — Michael D Abreu
(74) *Attorney, Agent, or Firm* — Vista IP Law Group LLP (57) ABSTRACT

Neurostimulators and methods of using neurostimulators are provided. The neurostimulator is implanted within a tissue pocket of a patient, and electrical energy is conveyed from the neurostimulator to stimulate a target tissue site remote from the tissue pocket. The neurostimulator has a case with which one or more electrodes are associated. The electrical energy is returned to the electrode(s) in a manner that prevents, or at least reduces, pocket stimulation that may otherwise occur due to the return of electrical energy to the case of the neurostimulator.

16 Claims, 9 Drawing Sheets

U.S. PATENT DOCUMENTS

| | | | |
|---|---|---|---|
| 2006/0116737 | A1 | 6/2006 | Libbus |
| 2006/0229687 | A1* | 10/2006 | Goetz et al. ............. 607/46 |
| 2008/0097529 | A1 | 4/2008 | Parramon et al. |
| 2008/0103559 | A1 | 5/2008 | Thacker et al. |
| 2008/0262566 | A1 | 10/2008 | Jaax |
| 2010/0125314 | A1 | 5/2010 | Bradley et al. |
| 2010/0152817 | A1* | 6/2010 | Gillbe ............. 607/72 |

OTHER PUBLICATIONS

Davies, T., et al., Do Permanent Pacemakers Need an Insulative Coating? Results of a Prospective Randomized Double-Blind Study, Pacing Clin Electrophysiol. Oct. 1997, 20:(10 Pt 1):2394-2397.

Yajima, T., MD. et al., Effects of muscle potential depression and muscle stimulation caused by different insulation coating configurations on cardiac pacemakers, J. Artif Organs (2005) 8:47-50.

Non-Final Office Action dated Jul. 12, 2011 in U.S. Appl. No. 12/630,633, filed Dec. 3, 2009, inventor: Michael A. Moffitt et al., (10 pages).

Office Action dated Jun. 17, 2011 in U.S. Appl. No. 12/629,814, filed Dec. 2, 2009, inventor: Michael A. Moffitt, (13pages).

PCT International Preliminary Report on Patentability (Chapter I of the Patent Cooperation Treaty) for PCT/US2009/066621, Applicant: Boston Scientific Neuromodulation Corporation, Form PCT/IB/326 and 373, dated Jun. 16, 2011 (11pages).

PCT International Search Report for PCT/US2009/066621, Applicant: Boston Scientific Neuromodulation Corporation, Form PCT/ISA/210 and 220, dated Jun. 30, 2010 (9 pages).

PCT Written Opinion of the International Search Authority for PCT/US2009/066621, Applicant: Boston Scientific Neuromodulation Corporation, Form PCT/ISA/237, dated Jun. 30, 2010 (9 pages).

Annex to Form PCT/ISA206 Communication Relating to the Results of the Partial International Search for PCT/US2009/066621, Applicant: Boston Scientific Neuromodulation Corporation, Form PCT/ISA/206, dated Feb. 26, 2010 (7 pages).

* cited by examiner

IMPLANTABLE NEUROSTIMULATORS HAVING REDUCED POCKET STIMULATION

RELATED APPLICATION

The present application is a divisional of U.S. patent application Ser. No. 12/629,814, filed on Dec. 2, 2009, which claims the benefit under 35 U.S.C. §119 of U.S. Provisional Patent Application Ser. No. 61/119,662, filed Dec. 3, 2008, which is incorporated hereby reference in its entirety.

FIELD OF THE INVENTION

The present inventions relate to tissue stimulation systems, and more particularly, to systems and methods for preventing or reducing inadvertent stimulation of tissue adjacent an implantable neurostimulator.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator (i.e., an implantable pulse generator (IPG)) implanted remotely from the stimulation site, but coupled either directly to the stimulation lead(s) or indirectly to the stimulation lead(s) via a lead extension. For example, in the context of SCS, the electrode lead(s) are typically implanted along the dura of the spinal cord, with the electrode lead(s) exiting the spinal column, where they can generally be coupled to one or more electrode lead extensions. The electrode lead extension(s), in turn, are typically tunneled around the torso of the patient to a subcutaneous pocket (typically in the chest or abdomen) where the neurostimulator is implanted.

The neurostimulation system may further comprise a handheld patient programmer to remotely instruct the neurostimulator to generate electrical stimulation pulses in accordance with selected stimulation parameters. The handheld programmer, which may take the form of a remote control (RC) may, itself, be programmed by a clinician, for example, by using a clinician's programmer (CP), which typically includes a general purpose computer, such as a laptop, with a programming software package installed thereon.

Thus, electrical pulses can be delivered from the neurostimulator to the stimulation electrode(s) to stimulate or activate a volume of tissue. In particular, electrical energy conveyed between at least one cathodic electrode and at least one anodic electrodes creates an electrical field, which when strong enough, depolarizes (or "stimulates") the neurons beyond a threshold level, thereby inducing the firing of action potentials (APs) that propagate along the neural fibers.

Electrical pulses may be delivered from the neurostimulator to the stimulator electrode(s) in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, and rate of the stimulation pulses.

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the magnitude, duration, and rate of the electrical current pulses. The stimulation regimen will typically be one that provides stimulation energy to all of the target tissue that must be stimulated in order to provide the therapeutic benefit, yet minimizes the volume of non-target tissue that is stimulated. In the case of SCS, such a therapeutic benefit is "paresthesia," i.e., a tingling sensation that is effected by the electrical stimuli applied through the electrodes.

Electrical energy may be transmitted to the tissue in a monopolar or multipolar (e.g., bipolar, tripolar, etc.) fashion. Monopolar delivery occurs when a selected one or more of the lead electrodes is activated along with the case of the neurostimulator, so that electrical energy is transmitted between the selected electrode and the case. Bipolar delivery occurs when two of the lead electrodes are activated as anode and cathode, so that electrical energy is transmitted between the selected electrodes. Tripolar delivery occurs when three of the lead electrodes are activated, two as anodes and the remaining one as a cathode, or two as cathodes and the remaining one as an anode.

. In the context of SCS, the neurostimulator case is used as a cathodic return electrode, and the lead electrodes are used as anodic stimulating electrodes. The neurostimulator case is selected as the cathodic return electrode, because it is relatively far away from the stimulation site, and because it has a large surface area, resulting in relatively small current densities.

This pocket stimulation problem is exacerbated when microstimulators are used. A "microstimulator" is an implantable neurostimulator in which the body or case of the device is compact (typically on the order of a few millimeters is diameter by several millimeters to a few centimeters in length). For example, the Bion® microstimulator (manufactured and distributed by Boston Scientific Neuromodulation Corporation) is a tiny fraction of the size of the Precision® IPG. Typically, the cases of the microstimulators carry electrodes for producing the desired electrical stimulation current. Microstimulators of this type (i.e., microstimulators with leadless electrodes) are implanted proximate to the target tissue to allow the stimulation current to stimulate the target tissue to provide therapy for a wide variety of conditions and disorders. In these cases, it is, of course, desired for the pocket in which the microstimulator is implanted to be stimulated.

However, it may sometimes be desirable to connect one or more short, flexible stimulation leads to a microstimulator, as described in U.S. patent application Ser. No. 09/624,120, filed Jul. 24, 2000, which is expressly incorporated herein by reference. The use of such leads may permit electrical stimulation to be directed more locally to target tissue a short distance from the microstimulator, while allowing the microstimulator to be located in a more surgically convenient site. In this case, stimulation of the implantation pocket is undesirable.

Because the case of a microstimulator is relatively small, the current density on the surface of the case may be quite high when the microstimulator is operated in a monopolar mode. For example, the surface area on the case of a Precision® IPG is 3882 mm², whereas the surface area of the anodic surface of the Bion® microstimulator is approximately 50 mm². If this anodic surface were used with a leaded Bion® microstimulator, undesired and perhaps annoying or painful stimulation in the implantation pocket might be expected.

Attempts have been made to prevent or, at least reduce, inadvertent pocket stimulation when operating a neurostimulator in a monopolar mode. For example, it is known to coat a portion of the neurostimulator case (e.g., the edges where current density is the greatest) with an insulative material in order to reduce pocket stimulation (see Toshimi Yajima, et al. "Effects of Muscle Potential Depression and Muscle Stimulation Caused by Different Insulation Coating Configurations on Cardiac Pacemakers: The Use of Insulative Coatings to Try to Reduce Pocket Stimulation," J Artif Organs (2005) 8:47-50; Davies T, "Do Permanent Pacemakers Need an Insulative Coating? Results of Prospective Randomized Double-Blind Study," Pacing Clin. Electrophysiol. 1997 October; 20(10 Pt 1):2394-7). However, coating a portion of the neurostimulator case necessarily increases the current density of the uncoated portions, thereby potentially increasing the chance that pocket stimulation will occur adjacent these higher current density sections. Furthermore, new edges are created between the coated and uncoated portions of the neurostimulator case, thereby creating higher current densities at these new edges.

There, thus, remains a need to provide an improved neurostimulator and technique that prevents, or at least, minimizes inadvertent pocket stimulation.

SUMMARY OF THE INVENTION

In accordance with one aspect of the present inventions, another method of providing therapy using a neurostimulator implanted within a tissue pocket of a patient is provided. The neurostimulator has a case and a plurality of electrodes associated with the case. The electrodes may form at least a portion of the case or may be separate elements that are disposed on the case. The method comprises conveying electrical energy from the neurostimulator (e.g., to at least one stimulation lead connected to the neurostimulator), thereby stimulating a target tissue site remote from the tissue pocket, and independently returning the electrical energy to the electrodes, e.g., to prevent inadvertent stimulation of the tissue pocket that would otherwise occur.

The electrical energy may be independently returned to the electrodes, e.g., by returning the electrical energy to the electrodes in a temporally interleaved fashion. In this case, the electrical energy may be pulsed electrical energy, such that a plurality of electrical pulses respectively returned to the electrodes are temporally interleaved. In one method, a single electrical pulse is conveyed from the neurostimulator to the target tissue site while a plurality of electrical pulses are respectively returned to the electrodes, such that each electrical pulse returned to the respective electrodes has a shorter duration than the single electrical pulse. Multiple electrical pulses can be returned to each of the electrodes while the single electrical pulse is conveyed from the neurostimulator. If the plurality of electrodes comprises at least three electrodes, the electrical energy can be serially returned to the electrode(s).

The electrical energy may be independently returned to the electrodes, e.g., by selectively activating the electrodes. In one method, the electrical energy can be simultaneously returned to the activated electrodes. In another method, the electrical energy returned to the electrodes can be independently adjusted, e.g., by selecting a fractionalized electrical current for the activated electrodes. In still another method, a portion of the electrical energy can be returned to at least one external lead connected to the neurostimulator.

In accordance with another aspect of the present inventions, a neurostimulator is provided. The neurostimulator comprises a case and a plurality of electrodes (e.g., segmented electrodes) associated with the case. The electrodes may form at least a portion of the case or may be separate elements that are disposed on the case. The neurostimulator further comprises one or more connectors configured for being coupled to one or more stimulation leads, and stimulation circuitry contained within the case. The stimulation circuitry is configured for conveying electrical energy to the stimulation lead(s), and independently returning the electrical energy to the electrodes, e.g., in the manner described above.

In accordance with another aspect of the present inventions, another neurostimulator is provided. The neurostimulator comprises a segmented case having a plurality of case sections (e.g., one having an edge and one having a smooth or flat surface with no edges), one or more connectors configured for being coupled to one or more stimulation leads, and stimulation circuitry contained within the segmented case. The stimulation circuitry has at least one terminal electrically coupled to the segmented case (either in parallel or in series), and is configured for conveying electrical energy to the stimulation lead(s), and returning the electrical energy to the segmented case.

The stimulation circuitry further comprises means for decreasing the variance of current densities (e.g., to 25% or less, or even 10% or less) on the segmented electrodes. The means may comprise different materials from which the case sections are respectively composed or at least one discrete passive component (e.g., a resistor) electrically coupled between the terminal(s) and at least one of the respective case sections. In the latter case, a plurality of discrete passive components having different impedances can be electrically coupled between the terminal(s) and the respective case sections.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
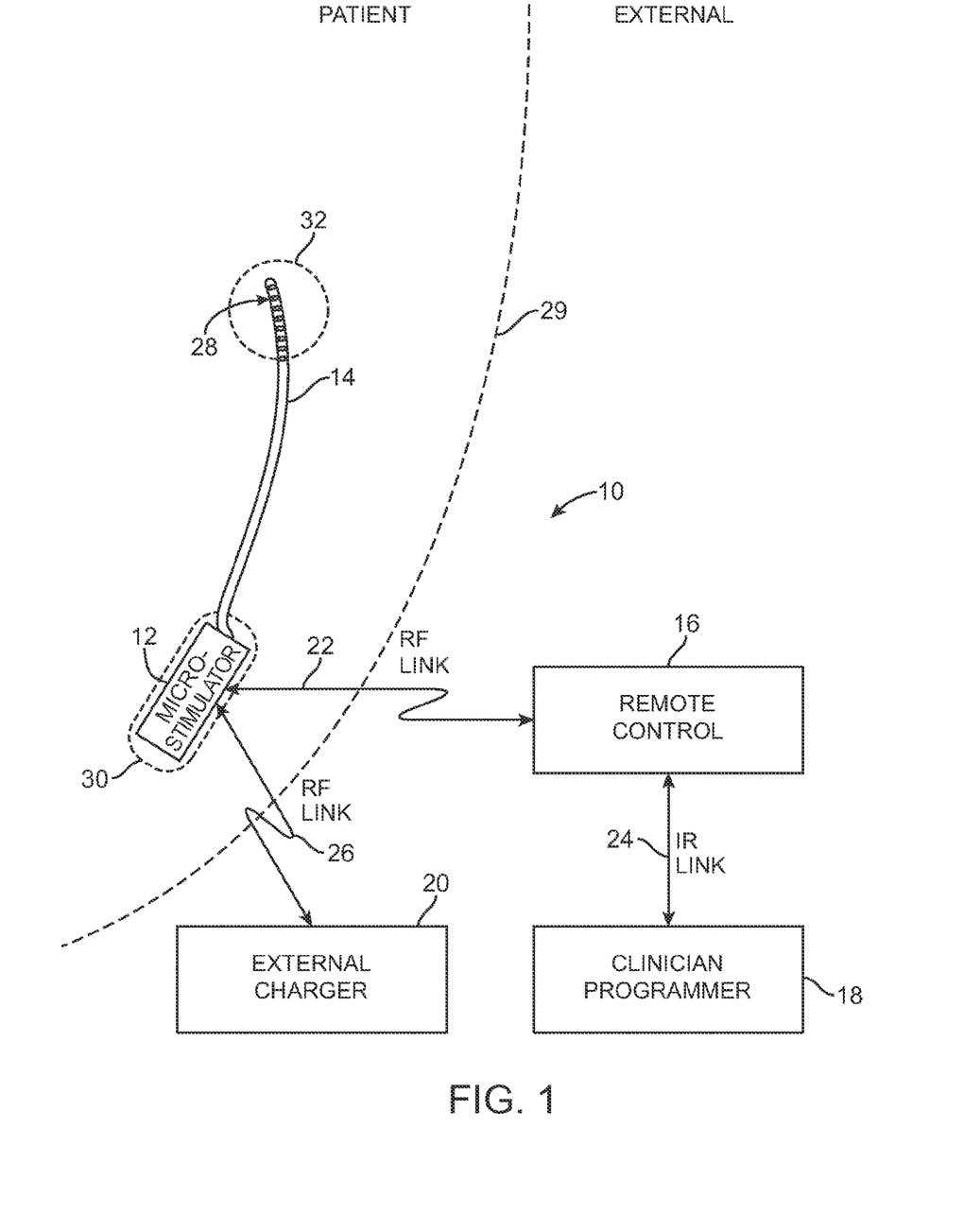
FIG. 1 is plan view of one embodiment of a tissue stimulation system arranged in accordance with the present inventions.

Turning first to FIG. 1, an exemplary tissue stimulation system 10 generally includes a neurostimulator, and in particular, a microstimulator 12, an implantable stimulation lead 14, an external control device in the form of a remote controller RC 16, and a clinician's programmer (CP) 18. The stimulation system 10 may also include an external trial stimulator (not shown) for testing the effects of the stimulation prior to implantation of the microstimulator 12, and an external charger 20 for recharging the microstimulator 12.

It should be noted that, although the neurostimulator is described as being a microstimulator herein, the present invention may be used with used with any type of implantable electrical circuitry used to stimulate tissue where it is desirable to prevent pocket stimulation. It should also be noted that, although the microstimulator 12 is described herein as being battery-powered, the microstimulator 12 alternatively be radio-frequency (RF)-controlled. Ultimately, the architecture of the microstimulator 12 will depend on the context in which it is intended to be used.

For example, for some patients, the use of a stimulator for only a few hours per day or week will improve the symptomatology of the ailment or ailments suffered by the patient. In such patients, RF-controlled devices provide an adequate amount of stimulation if used intermittently, e.g., for only a few hours per day, to greatly decrease the incidence of the symptoms. For many other patients, however, a continuous or intermittent stimulation throughout the day is needed. These patients may best utilize a stimulator that has a self-contained power source sufficient to deliver stimulation for several hours and that can be recharged repeatedly, if necessary. Thus, the use of a stimulator with a rechargeable battery, thus, provides these patients the portability needed to free the patient from reliance on RF power delivery.

For purposes of the specification, it is sufficient to note that RF-controlled stimulators receive power and control signals from an extracorporeal device via inductive coupling of a modulated RF field. Battery-powered stimulators incorporate a power source within the device itself, but rely on RF control, inductive linking, or the like to program stimulus sequences and to recharge the power source, when needed. Whether RF-controlled or battery-powered the implanted stimulator may be commanded to generate pulsed electrical stimulation energy (i.e., a temporal series of electrical pulses) in accordance with a set of stimulation parameters, including pulse amplitude, pulse width, pulse rate, etc. Further details discussing battery-powered stimulators are disclosed in PCT Publication WO 98/37926, WO 98/43700, and WO 98/43701, and U.S. Patent Publication No. 2008/0097529, which are expressly incorporated herein by reference.

Thus, once the microstimulator 12 and stimulation lead 14 are implanted, the RC 16 may be used to telemetrically control the IPG 14 via a bi-directional RF communications link 22. Such control allows the microstimulator 12 to be turned on or off and to be programmed with different stimulation parameter sets. The RC 16 may also be operated to modify the programmed stimulation parameters to actively control the characteristics of the electrical stimulation energy output by the microstimulator 12.

The CP 18 provides clinician detailed stimulation parameters for programming the microstimulator 12 in the operating room and in follow-up sessions. The CP 18 may perform this function by indirectly communicating with the microstimulator 12, through the RC 16, via an IR communications link 24. Alternatively, the CP 18 may directly communicate with the microstimulator 12 via an RF communications link (not shown). The external charger 20 is a portable device used to transcutaneously charge the microstimulator 12 via an inductive link 26. Once the microstimulator 12 has been programmed, and its power source has been charged by the external charger 20 or otherwise replenished, the microstimulator 12 may function as programmed without the RC 16 or CP 18 being present.

The stimulation lead 14 carries a plurality of electrodes 28 arranged in an array. In the illustrated embodiment, the stimulation lead 14 is a flexible percutaneous lead, and to this end, the electrodes 28 are arranged in-line along the stimulation lead 14. In the illustrated embodiment, the stimulation lead 14 includes four collinear electrodes 28, but may include as little as two electrodes 28 and as many as sixteen or more electrodes 28. In alternative embodiments, the electrodes 28 may be arranged in a two-dimensional pattern on a single paddle lead. The electrodes 28 may be composed of a noble or refractory metal or compound, such as platinum, iridium, tantalum, titanium, titanium nitride, niobium, or alloys thereof, in order to avoid corrosion or electrolysis, which could damage the surrounding tissues and/or stimulation lead 14.

The use of the stimulation lead 14 permits electrical stimulation to be directed more locally to targeted tissue sites a short distance from the tissue pocket in which the microstimulator 14 will be implanted. In one embodiment, the leads are no longer than 120 mm. The stimulation lead 14 is preferably less than 5 mm in diameter, and more preferably less than 1.5 mm in diameter. The stimulation lead 14 further comprises a proximal connector (not shown) and wires (not shown) electrically connecting the electrodes 28 to the proximal connector. Further details regarding the use of stimulation leads with microstimulators are disclosed in U.S. patent application Ser. No. 09/624,130, filed Jul. 24, 2000, which is expressly incorporated herein by reference.

As shown in FIG. 1, a single microstimulator 12 and stimulation lead 14 are implanted under the skin 29 of the patient, with the microstimulator 12 disposed into a subcutaneous pocket 30, and the electrode array 28 of the stimulation lead 14 disposed at a target tissue site 32 remote from the subcutaneous pocket 30. Nerve bundles at the target tissue site 32 may carry somatic sensor axons supplying receptors in skin and muscle and somatic motor axons supplying skeletal muscle, as well as autonomic axons supplying visceral and glandular structures and smooth muscle. In alternative techniques, multiple microstimulators 12 with respective stimulation leads 14 or a single microstimulator 12 with multiple stimulation leads 14 may be implanted to achieve greater stimulation of the target tissue site 32.

The microstimulator 12 may be implanted into the patient with a surgical insertion tool specifically designed for this purpose, as described in U.S. Pat. No. 6,582,441, which is expressly incorporated herein by reference, or may be placed, for example, via a small incision and through a small cannula. Alternatively, the microstimulator 12 may be implanted via conventional surgical methods, or may be inserted using other endoscopic or laparoscopic techniques. A more complicated surgical procedure may be required for the purposes of fixing the microstimulator 12 in place. The stimulation lead 14 may be implanted into the patient using suitable means, such as an endoscope or laparoscope, and mated to the microstimulator 12.

Figure 2:
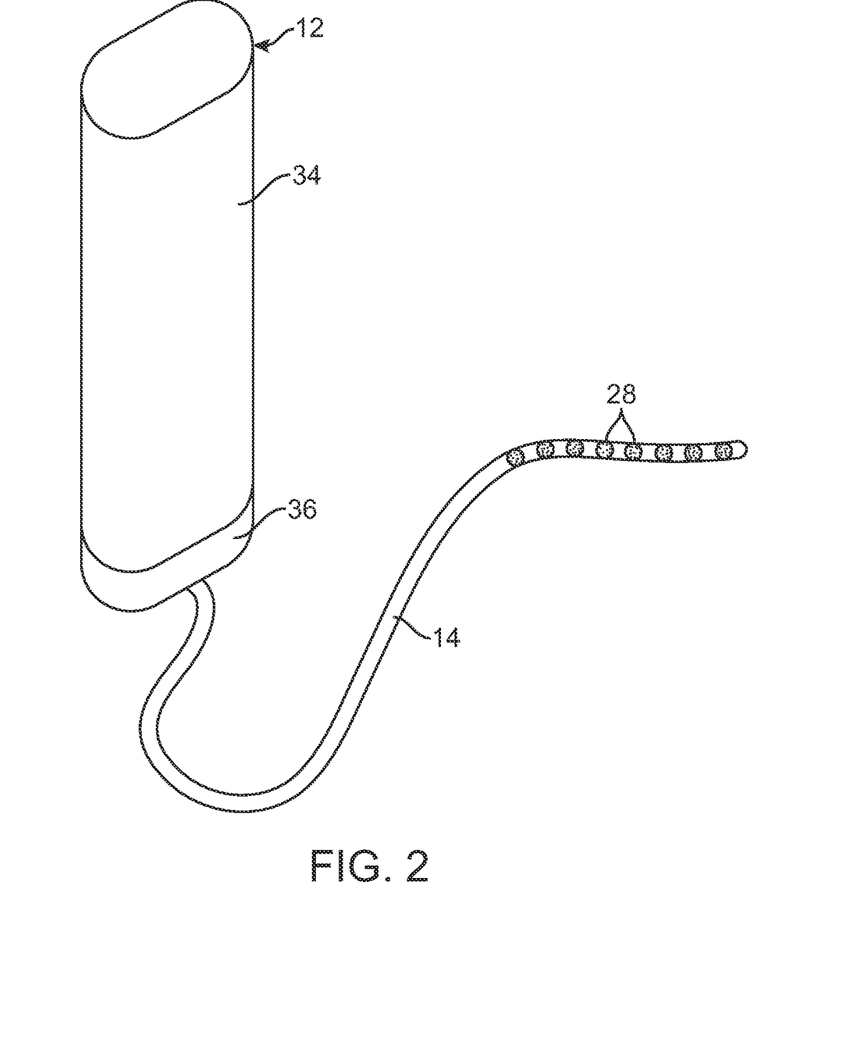
FIG. 2 is a perspective view of a microstimulator used in the tissue stimulation system of FIG. 1.

Referring now to FIG. 2, the microstimulator 12 includes a case 34 and electronic circuitry 38 (shown in FIG. 3) contained within the case 34. A preferred microstimulator 12 is sufficiently small to permit its placement near structures with very little discomfort. As such, the case 34 may have an area equal to or less than 1000 $mm^2$, and preferably, less than 200 $mm^2$, and may have a diameter less than 5 mm and a length less than 35 mm. The shape of the microstimulator 12 may be determined by the structure in which it will be implanted, the surrounding area, and the method of implantation. In the illustrated embodiment, the case 34 takes the form of a narrow, elongated body with an oblong cross-section, but other shapes, such as rounded cylinders, spheres, disks, and helical structures, are possible. The outer case 34 is composed of an electrically conductive, biocompatible material, such as titanium, and forms a hermetically sealed compartment wherein the internal electronics are protected from the body tissue and fluids. In the illustrated embodiment, the case 34 or a portion thereof may serve as an electrode.

Figure 3:
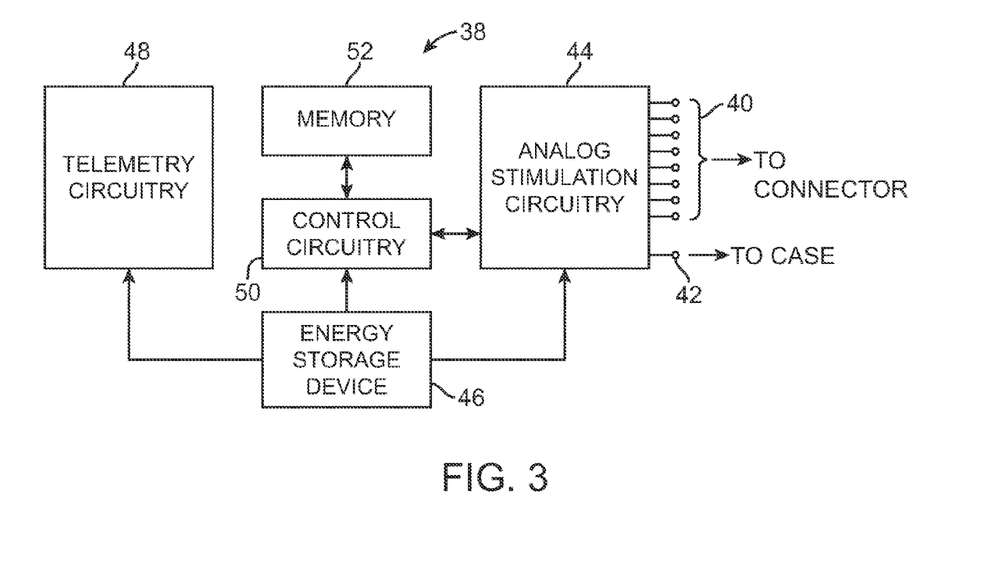
FIG. 3 is a block diagram of the electronic circuitry contained within the microstimulator of FIG. 2.

The microstimulator 12 further includes a connector 36 to which the proximal end of the stimulation lead 14 can be mated, thereby electrically coupling the electronic circuitry to the electrode array 28. In particular, as shown in FIG. 3, the electronic circuitry 38 is also electrically coupled to the connector 36 via one or more output terminals 40 (in this case, eight terminals for the eight electrodes), and electrically coupled to the case 34 via one or more electrical terminals 42 (in this case, a single terminal), so that the electrical energy can be conveyed to the electrodes 28, and thus, the tissue target site 32, and then returned at the case 34.

The electronic circuitry 38 further includes analog stimulation circuitry 44 in the form of pulse generation circuitry that delivers the electrical stimulation energy in the form of a pulsed electrical waveform to the electrode array 28 in accordance with a set of stimulation parameters. Such stimulation parameters may comprise electrode combinations, which define the electrodes (including the case 34) that are activated as anodes (positive), cathodes (negative), and turned off (zero), and electrical pulse parameters, which define the pulse amplitude (measured in milliamps or volts depending on whether the microstimulator 12 supplies constant current or constant voltage to the electrode array 28), pulse duration (or pulse width) (measured in microseconds), and pulse rate (measured in pulses per second).

The stimulation circuitry 44 may, e.g., include a single current or voltage source (not shown) for conveying stimulation energy to selected ones of the electrodes 28 as a group and returning the stimulation energy to selecting ones of the electrodes as a group, or multiple current or voltage sources (no shown) for independently conveying stimulation energy to selected ones of the electrodes and independently returning the stimulation energy to selected ones of the electrodes.

In any event, electrical stimulation will occur between two (or more) activated electrodes, one of which may be the case 34. Simulation energy may be transmitted to the tissue in a monopolar or multipolar (e.g., bipolar, tripolar, etc.) fashion. Monopolar stimulation occurs when selected ones of the lead electrodes 28 are activated along with the case 34 of the microstimulator 12, so that stimulation energy is transmitted between the selected lead electrodes 28 and the case 34. Bipolar stimulation occurs when two of the lead electrodes 28 are activated as anode and cathode, so that stimulation energy is transmitted between the selected electrodes 28. Tripolar stimulation occurs when three of the lead electrodes 28 are activated, two as anodes and the remaining one as a cathode, or two as cathodes and the remaining one as an anode. Thus, when the microstimulator 12 is operated in a monopolar mode, the stimulation circuitry 44 will convey electrical stimulation energy to the lead electrodes 28 and return the electrical stimulation to the case 34. When the microstimulator 12 is operated in a multipolar mode, the stimulation circuitry 44 will convey electrical stimulation energy to lead electrodes 28 and return the electrical stimulation energy at different lead electrodes 28.

In the illustrated embodiment, when the microstimulator 12 is operated in the monopolar mode, the electrical energy that is conveyed from the microstimulator 12 to the target tissue site is cathodic (i.e., the activated lead electrodes 28 are cathodes), and the electrical energy returned to the case 34 of the microstimulator 12 is anodic (i.e., the case 34 serves as an anode). However, the assignment of anodic and cathodic current to the lead electrodes 28 and case 34 will ultimately depend on the application in which the system 10 is intended to use. That is, if the nerve fibers at the target tissue site 32 are to be stimulated with cathodic current, the lead electrodes 28 will be cathodes and the case 34 will be an anode. On the other hand, if the nerve fibers at the target tissue site 32 are to be stimulated with anodic current, the lead electrodes 28 will be anodes and the case 34 will be a cathode. In any event, the lead electrodes 28 and the case 34 will be oppositely polarized.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

In the illustrated embodiment, the microstimulator 12 is battery-powered, and thus, the electronic circuitry 38 includes an energy storage device 46; for example, a replenishable or rechargeable battery, such as a lithium ion battery, an electrolytic capacitor, a super- or ultra-capacitor, or the like). If the energy storage device 46 is replenishable or rechargeable, an external charger (not shown) can be used to charge the power source via an inductive link. The energy storage device 46 is configured to output a voltage used to supply the various components of the electronic circuitry 38 with power. The energy storage device 46 also provides power for any stimulation current generated by the stimulation circuitry 44.

The microstimulator 12 further comprises telemetry circuitry 48 (which includes an antenna in the form of an inductive coil and transceiver) for receiving programming data (including stimulation parameters), transmitting status data to and from the remote controller 16, and receiving power from an external device, which may be the remote controller 16. The microstimulator 12 further comprises control circuitry 50 (which may be embodied in an integrated circuitry (IC) chip) for operating the stimulation circuitry 44 in accordance with a set or sets of stimulation parameters (e.g., selection of activated electrodes, pulse amplitude, pulse width, pulse rate, etc.), and a memory 52 for storing the stimulation parameters. The memory 52 may be any type of memory unit, such as, but not limited to, random access memory (RAM), status RAM (SRAM), EEPROM, a hard drive, or the like. Thus, the use of the control circuitry 50 and memory 52 allow the stimulation parameters to be adjusted to setting that are safe and efficacious with minimal discomfort for each individual. Specific stimulation parameters may provide therapeutic advantages for different patients or for various types and classes of ailments. For instance, some patients may respond favorably to intermittent stimulation, while others may require continuous stimulation for treatment and relief.

In addition, different stimulation parameters may have different effects on different tissue. Therefore, stimulation parameters may be chosen to target specific neural or other cell populations and/or to exclude others, or to increase activity in specific neural or other cell populations, and/or to decrease activity in others. For example, a relatively low pulse rate (i.e., less than 100 pulses per second (pps)) may have an excitatory effect on surrounding neural tissue, leading to increased neural activity ("excitatory stimulation"), whereas a relatively high pulse rate (i.e., greater than 100 pps) may have an inhibitory effect, leading to decreased neural activity ("inhibitory stimulation"). As another example, a relatively low pulse amplitude (typically less than 15 mA), but dependent on the distance between electrodes and nerve fibers) are likely to recruit relatively large diameter fibers (e.g., A-α and/or A-β fibers), while not recruiting relatively small diameter fibers (e.g., A-δ and/or C fibers). In the illustrated embodiment, the pulse rate may be in the range of 2-20 pps, the pulse duration may be in the range of 50-350 microseconds, and the amplitude may be in the range of 1-5V at about 1-50 mA.

Significant to the present inventions, the microstimulator 12 is designed in a manner that prevents, or at least reduces, the pocket stimulation phenomenon when operated in a monopolar mode.

For example, in the case where the nerve fibers stimulated in the tissue pocket 30 are smaller than the nerve fibers stimulated at the target tissue site 32 for therapy, stimulation energy having relatively short pulse widths might be used to selectively stimulate the larger nerve fibers at the target tissue site 32 without stimulating the smaller nerve fibers at the tissue pocket 30. The difference between the amplitude at which smaller nerve fibers are stimulated and the amplitude at which large nerve fibers are stimulated allows the amplitude of the electrical energy to be adjusted within a usage range where the larger nerve fibers at the target tissue site 32 are stimulated, while the smaller nerve fibers at the tissue pocket 30 are not stimulated. Reducing the pulse width of the electrical stimulation effectively increases this usage range.

Figure 4:
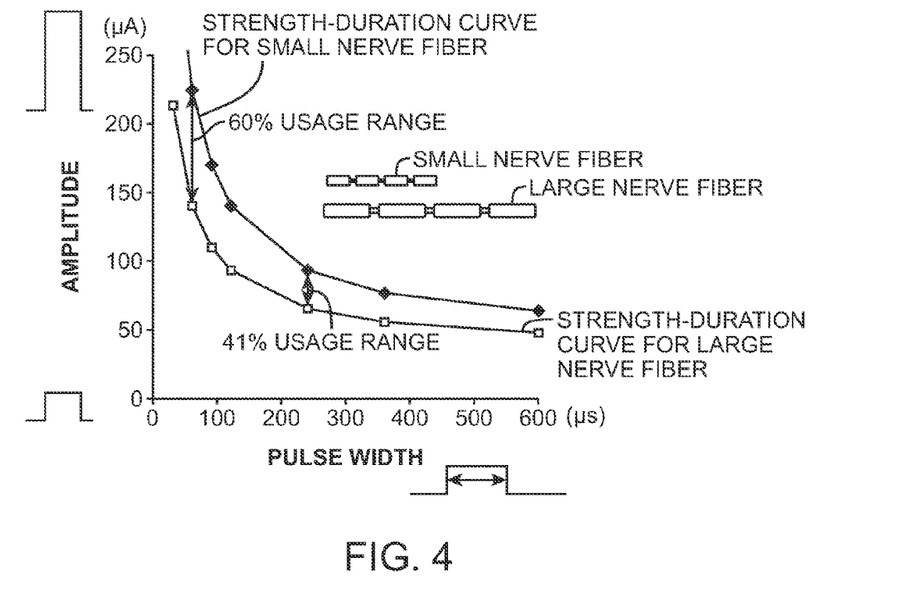
FIG. 4 is a plot of strength-duration curves for an exemplary small nerve fiber and an exemplary large nerve fiber.

The benefits of this technique can be better appreciated with reference to FIG. 4, which illustrates the strength-duration curves for smaller nerve fibers (solid line) and larger nerve fibers (dashed line). Notably, a strength-duration curve represents the pulse amplitude and pulse width needed to stimulate a nerve fiber of a specified diameter, and the usage range with respect to the strength-duration curve is the variance from the strength-duration curve that maintains the stimulation energy between the point at which it is perceived by the patient (i.e., the point at which stimulation at the tissue target site 32 (shown in FIG. 1) is perceived) and the point at which it is uncomfortable for the patient (i.e., the point at which stimulation at the tissue pocket 30 is perceived). It should be noted that at shorter pulse widths, the usage range between large and small nerve fibers is greater (assuming a pulse width of 50 μs, the usage range is 60% of the amplitude that stimulates the large nerve fibers) than the usage range between larger and small nerve fibers (assuming a pulse width of 250 μs, the usage range is 41% of the amplitude that stimulates the large nerve fibers). It follows from this that using stimulation energy with small pulse widths is more selective, and therefore, can be more easily used to avoid stimulation of the relatively small nerve fibers in the tissue pocket 30 (shown in FIG. 1), while stimulation energy with larger pulse widths is not as selective, and therefore, more difficult to avoid stimulation of the relatively small nerve fibers in the tissue pocket 30.

In one exemplary manner that uses stimulation energy with smaller pulsewidths to avoid pocket stimulation, pulsed electrical energy is initially conveyed from the microstimulator 12 to the lead electrodes 28, thereby stimulating the target tissue site 32 remote from the tissue pocket 30. The initially conveyed pulsed electrical energy is then returned to the case 34 of the neurostimulator, potentially causing stimulation of the tissue pocket 30. If stimulation of the tissue pocket 30 is detected (e.g., by the patient experiencing discomfort in that region and relaying this information to the clinician), the pulse width of the stimulation energy is decreased (e.g., in the range of 10-100 μs, and preferably equal or less than 50 μs).

The pulsed electrical energy is subsequently conveyed from the microstimulator 12 to the lead electrodes 28, thereby stimulating the target tissue site 32 again. The step of subsequently conveying the pulsed electrical energy may be performed by simply continuing the conveyance of the initially electrical energy or by ceasing conveyance of the pulsed electrical energy and then again conveying the pulsed electrical energy. In any event, the subsequently conveyed pulse electrical energy is then returned to the case 34 of the microstimulator 12 again. For the purposes of this specification, the term "initial" with reference to electrical energy conveyance does not necessarily mean the first time the electrical energy is conveyed by the microstimulator 12, but rather merely presupposes that there will be a subsequent conveyance of electrical energy.

Because the subsequently conveyed electrical energy is more selective than the initially conveyed electrical energy due to the decreased pulse width, stimulation of the tissue pocket 30 will be decreased, if not eliminated altogether. The pulse width of the stimulation energy can be further decreased to prevent stimulation of the tissue pocket 30 if not already eliminated. It should be noted that, as illustrated in the strength-duration curves in FIG. 4, the point at which a nerve fiber at a specific size is stimulated increases as the pulse width of the stimulation energy decreases, thereby potentially losing stimulation of the target tissue site 32 if adjustments in the amplitude are not made.

As a result, it may be desirable to increase the amplitude of the stimulation energy as the pulse width of the stimulation energy is decreased. Adjustment of the pulsewidth and amplitude of the stimulation energy can be manually performed via operation of the remote controller 16 or automatically performed, such as described in U.S. patent application Ser. No. 11/553,447, entitled "Method of Maintaining Intensity Output While Adjusting Pulse Width or Amplitude" and U.S. patent application Ser. No. 12/606,050 entitled "System and Method for Automatically Adjusting Pulse Parameters to Selectively Activate Nerve Fibers," which are expressly incorporated herein by reference.

Figure 5:
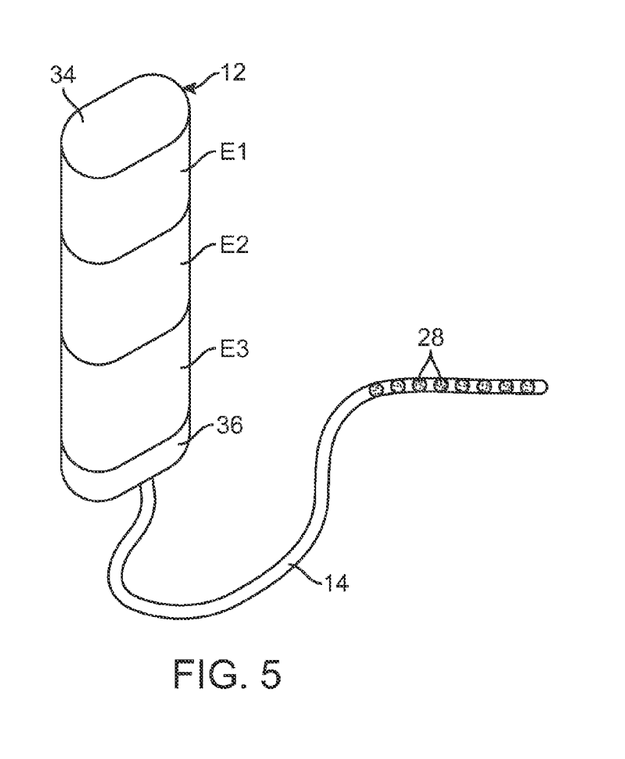
FIG. 5 is a perspective view of one embodiment of the microstimulator of FIG. 2 that can be operated to reduce pocket stimulation.

As another example of preventing pocket stimulation, the microstimulator 12 may be provided with spatially segmented electrodes (in this case, three electrodes E1-E3) that are associated with the case 34, as shown in FIG. 5. Although the case electrodes E1-E3 are illustrated as completely covering the outer surface of the case 34, the electrodes E1-E3 can be disposed on or form only a portion of the outer surface of the case 34. The microstimulator 12 is configured to independently return the pulsed electrical energy to the respective electrodes, thereby reducing or preventing inadvertent stimulation of the tissue pocket 30 (shown in FIG. 1).

Figure 7:
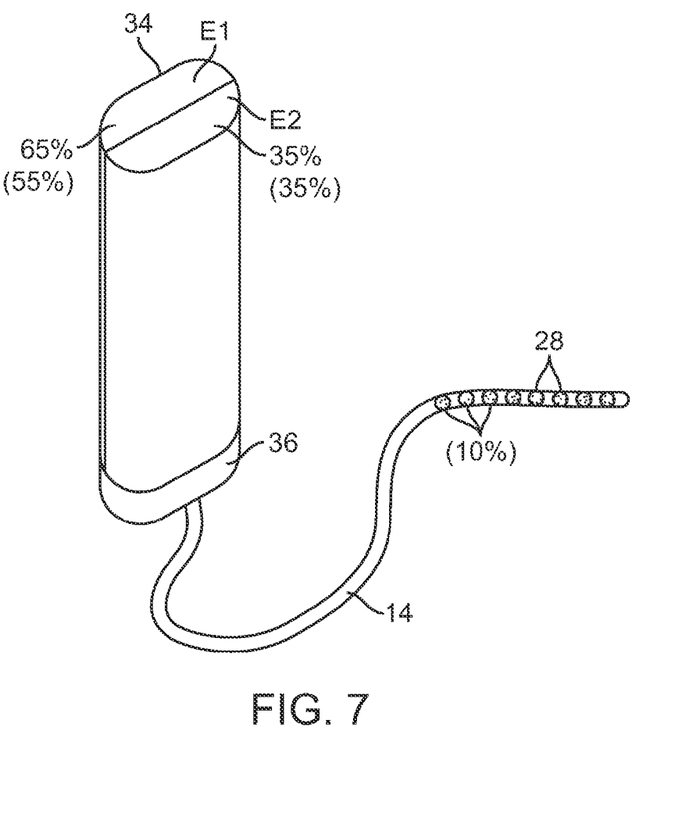
FIG. 7 is a perspective view of another embodiment of the microstimulator of FIG. 2 that can be operated to reduce pocket stimulation.

The electrodes E1-E3 may form the structure of the case 34 itself, or may be formed of electrically conductive and biocompatible material mounted to the outside of the case 34. The shape of the electrodes 28 may, e.g., be ring-shaped, as shown, or radial or disk-like. Ultimately, the shape of the electrodes 28 will depend upon the shape of the case 34. Although three ring-shaped electrodes E1-E3 are shown to form the case 34 illustrated in FIG. 5, a different number of electrodes with different shapes can be used. For example, as shown in FIG. 7, the same-shaped case 34 is used, but two electrodes E1-E2 can form the two halves of the case 34 that are coupled together in a clam-shell arrangement.

Figure 6:
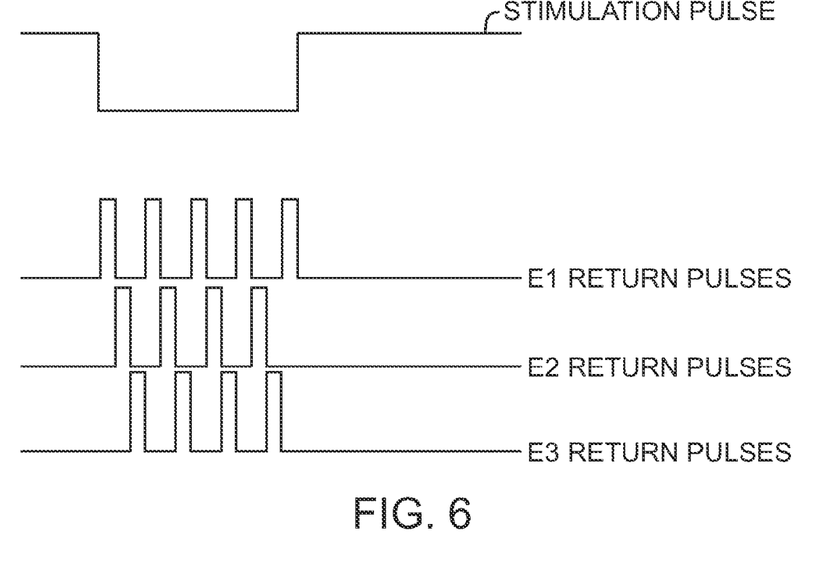
FIG. 6 is a plot of a stimulation pulse and temporally spaced return pulses that can be generated by the microstimulator of FIG. 5 to reduce the pocket stimulation.

In one technique for independently returning electrical energy to the case electrodes 28, a temporally segmented current waveform can be used. In particular, the electrical pulses returned to the respective electrodes 28 are temporally interleaved, as shown in FIG. 6. For example, for each stimulation pulse delivered to the lead electrodes 28, a pulse or a train of pulses can be returned to the first case electrode E1, then a pulse or a train of pulses can be returned to the second case electrode E2, and then a pulse or a train of pulses can be returned to the third case electrode E3. In this case, each return pulse necessarily has a shorter duration than the stimulation pulse. The pulses can be sequentially returned to the electrodes E1-E3, as shown in FIG. 6, or alternatively, can be randomly returned to the electrodes E1-E3. This process can be repeated for the same stimulation pulse, such that multiple pulses can be returned, as illustrated in FIG. 6.

It can be appreciated that the foregoing technique minimizes temporal summation of voltage at or across the neural membranes by virtue of the temporal spacings of the return pulses, and minimizes spatial summation of the voltage at or across the neural membranes by virtue of spacing of the electrodes 28. In alternative embodiments, any of the lead electrodes 28, in combination with the case electrodes 28, can be used to return the electrical energy.

In another technique for independently returning electrical energy to the case electrodes, the case electrodes are selectively activated; for example, via operation of the remote controller 16, thereby changing the electrical field within the tissue pocket 30 (shown in FIG. 1). Thus, the combination of case electrodes that reduces or eliminates the pocket stimulation can be selected. For example, electrical energy can be conveyed to the lead electrodes 28 and returned to the case 34 for different combinations of activated case electrodes. Based on patient feedback, the combination of case electrodes with the best result can then be selected as the return electrodes.

If the stimulation circuitry 44 of the microstimulator 12 (shown in FIG. 3) only comprises a single current or voltage source, the relative currents returned to the activated case electrodes cannot be controlled. However, if multiple current or voltage sources are provided, the fractionalized currents returned to the activated case electrodes can be controlled. For example, as shown in FIG. 7, one case electrode E1 can return 65% of the current, and another case electrode E2 can return 35% of the current.

In alternative embodiments, selected ones of the lead electrodes 28, in combination with the activated case electrodes E1-E2, can be used to return the electrical energy. In this case, only a portion of the electrical energy is returned to the case electrodes E1-E2. For example, the return current can be split 55%, 35%, and 10% between a selected case electrode E1, another selected case electrode E2, and a selected lead electrode 28, respectively.

Figure 8:
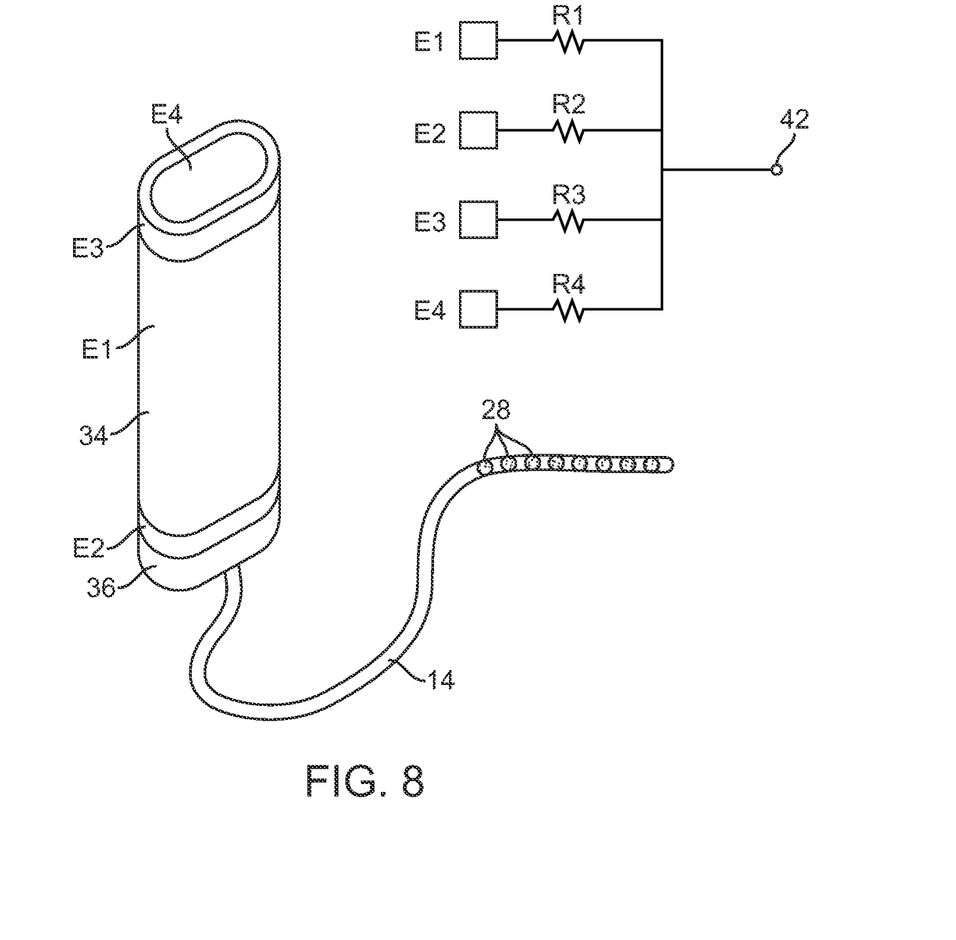
FIG. 8 is a perspective view of still another embodiment of the microstimulator of FIG. 2 that can be operated to reduce pocket stimulation.

As another example of preventing pocket stimulation, segmented electrodes can be associated with the case 34 of the microstimulator 12 in the same manner described above with respect to FIGS. 5 and 7. In this case, however, four electrodes are provided, as shown in FIG. 8, with electrode E1 forming the main body of the case 34, electrode E2 forming the bottom edge of the case 34 that meets the connector 36, electrode E3 forming the top edge of the case 34, and electrode E4 forming the flat top surface of the case 34.

Because geometrical features, such as corners and edges (e.g., the electrodes E2 and E3), are known to exhibit higher current densities as opposed to other geometrical features, such as smooth or flat surfaces (e.g., the electrodes E1 and E4), these higher current density regions may be more likely to cause stimulation than the other regions of the case 34. Thus, the current densities on the case electrodes E1-E4 are made as uniform as possible by decreasing the variances of the current densities to a relatively low value, (e.g., 25% or less, and preferably 10% or less). As a result, the maximum current density on the case electrodes E1-E4 is minimized, thereby minimizing or completely eliminating pocket stimulation.

The current densities on the case electrodes E1-E4 can be made more uniform by varying the relative impedances of the case electrodes E1-E4, with the electrodes that normally have higher current densities (e.g., electrodes having edges and corners, such as electrodes E2 and E3) having a relatively higher impedance, and the electrodes that normally have lower current densities (e.g., the electrodes having smooth or flat surfaces, such as electrodes E1 and E4) having a relatively lower impedance. For example, FIG. 8 illustrates a circuit representation of the case electrodes E1-E4 and associated impedances R1-R4. As there shown, the input terminal 42 of the stimulation circuitry 44 (shown in FIG. 3) is coupled in parallel to the four case electrodes E1-E4. It should be noted, however, that the input terminal 42 can alternatively be coupled in series to the four case electrodes E1-E4.

The relative impedances of the case electrodes E1-E4 can be changed, e.g., by making the electrodes from materials with different resistivities. For example, the edge electrodes E2, E3 may be composed of a material that has a higher resistivity than that of the flatter body and top electrodes E1, E4, thereby decreasing the current density exhibited by the edge electrodes E2, E3 relative to the current density that they would have exhibited had they been made of the same material as the body and top electrodes E1, E4.

As another example, passive components (not shown), such as resistors, can be located between the input terminal 42 of the stimulation circuitry 44 and the particular case electrodes, such as the edge electrodes E2, E3, with the anticipated higher current densities. In this manner, the passive components decrease the current density on the edge electrodes E2, E3 relative to the current density that would have been on the electrodes E2, E3 absent the passive components. Alternatively, passive components can be located between the input terminal 42 of the stimulation circuitry 44 and all four case electrodes E1-E4, with the combined resistance value of the passive component or components associated with each of the electrodes increasing with the anticipated current density.

Although the case electrodes E1-E4 have been described as being coupled to a single input terminal 42, in alternative embodiments, the case electrodes E1-E4 can be respectively coupled to a plurality of input terminals. In this case, if the stimulation circuitry 44 comprises multiple current or voltage sources, the electrical currents at the respective input terminals can be independently adjusted by increasing or decreasing the current or voltage of the sources. For example, for the edge electrodes E2, E3 (i.e., the case electrodes where a high current density is anticipated), the electrical current at the respective input terminals coupled to these electrodes can be set to be relatively low, whereas for the flat or smooth electrodes E1, E4 (i.e., the case electrodes where a low current density is anticipated), the electrical current at the respective input terminals coupled to these electrodes can be set to be relatively high.

As another example of preventing pocket stimulation, the current density on the case electrode(s) can be reduced by using an external lead with additional electrodes that are not intended for stimulation therapy. In this case, the electrical energy is conveyed from the microstimulator 12 to the lead electrodes 28, thereby stimulating the target tissue site 32 remote from the tissue pocket 30 (shown in FIG. 1), while the conveyed electrical energy is returned to both the case electrode(s) and the external lead.

Figure 9A:
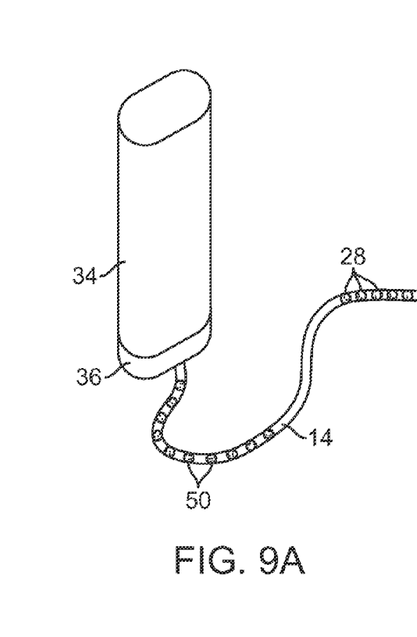
FIGS. 9A-9C are perspective views of other embodiments of the microstimulator of FIG. 2 that can be operated to reduce pocket stimulation.

For example, in one embodiment illustrated in FIG. 9A, the stimulation lead 14, itself, serves as the external lead, with additional electrodes 50 located on the proximal end of the stimulation lead for returning the electrical energy along with the case electrode(s). In another embodiment illustrated in FIG. 9B, an external lead 52 that is separate from the stimulation lead 14 is provided. In still another embodiment, an external lead 54 in the form of an electrical conductor is used to return the electrical energy along with the case electrode(s). The electrical conductor 54 could, e.g., be composed of a flexible or rigid hypotube or wire composed of a biocompatical, electrically conductive, material, such as stainless steel or platinum. If the electrical conductor 54 is made from a hypotube, it can be etched for flexibility.

Figure 9B:
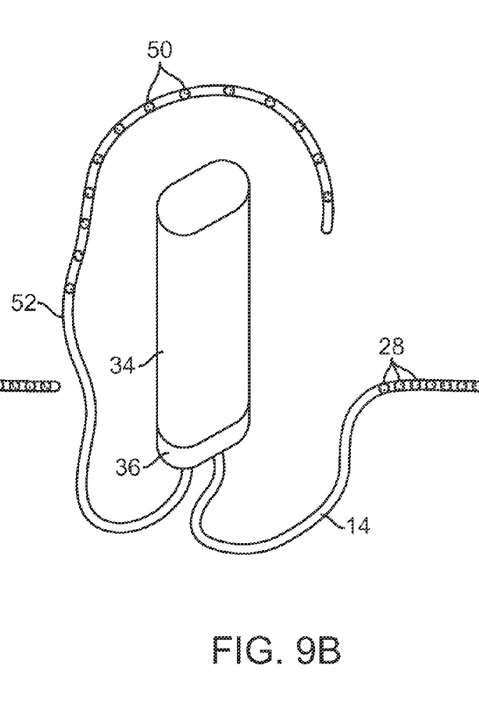
Figure 9C:
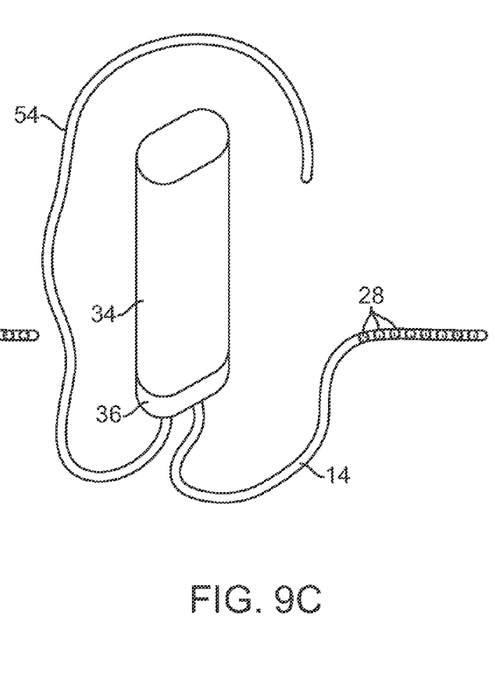

In either of the embodiments in FIGS. 9A-9C, the additional electrodes 50 can be directly electrically coupled to the case 34 via the connector 36, thereby reducing the current density on the case electrode(s). For the purposes of this specification, an element is directly electrically coupled to another element if no active components are located between the elements. In the embodiments of FIGS. 9A and 9B, the electrodes 50 can be ganged together using a common lead conductor (not shown). Alternatively, any of the additional electrodes 50 can be electrically coupled to input terminals of the stimulation circuitry 42 that are not already used to return electrical energy from the case electrodes. In this case, selected ones of the additional electrodes 50 may be activated in the case where the stimulation circuitry 42 has a switch and/or fractionalized currents can be assigned to the activated electrodes 50 in the case where the stimulation circuitry 42 includes multiple current or voltage sources.

As another example of preventing pocket stimulation, the current density on the case electrode(s) can be reduced by using an external lead with additional electrodes that are not intended for stimulation therapy. In this case, the electrical energy is conveyed from the microstimulator 12 to the lead electrodes 28, thereby stimulating the target tissue site 32 remote from the tissue pocket 30 (shown in FIG. 1), while the conveyed electrical energy is returned to both the case electrode(s) and the external lead.

As another example of preventing pocket stimulation, the current density on the case electrode(s) can be reduced by using an expandable electrode that, like the previous embodiment, is not intended for stimulation therapy. In this case, the electrical energy is conveyed from the microstimulator 12 to the lead electrodes 28, thereby stimulating the target tissue site 32 remote from the tissue pocket 30 (shown in FIG. 1), while the conveyed electrical energy is returned to both the case electrode(s) and the expandable electrode.

Figure 10A:
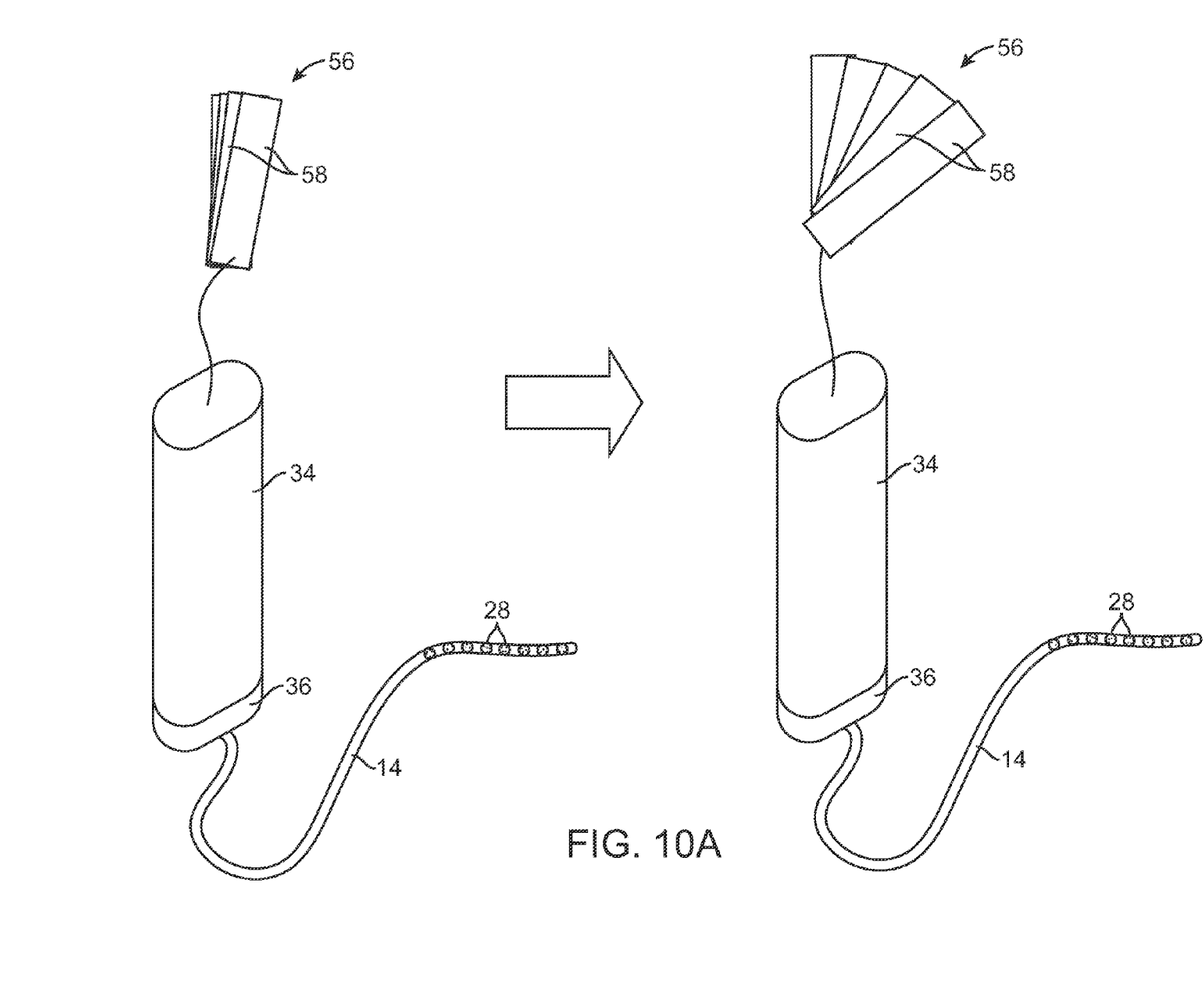
FIGS. 10A-10B are perspective views of still other embodiments of the microstimulator of FIG. 2 that can be operated to reduce pocket stimulation.

For example, in one embodiment illustrated in FIG. 10A, an expandable electrode 56 is directly electrically coupled to the top of the case 34 via a conductor 58, and is therefore used to return electrical energy along with the case electrode(s). To allow for its expansion, the electrode 56 includes a plurality of stacked blades 58 that are tied together at one end. When the electrode 56 is in a non-expanded geometry, the stacked blades 58 are folded together (left side of FIG. 10A), so that it can be easily introduced into the patient's body during implantation. To place the electrode 56 in an expanded geometry, the stacked blades 58 are radially folded out, much like a fan (right side of FIG. 10A), thereby increasing the surface area of the electrode 56 after implantation. In the illustrated embodiment, the shape of the blades 58 is rectangular, although other shapes may be used, including those with rounded edges or triangular shapes.

Figure 10B:
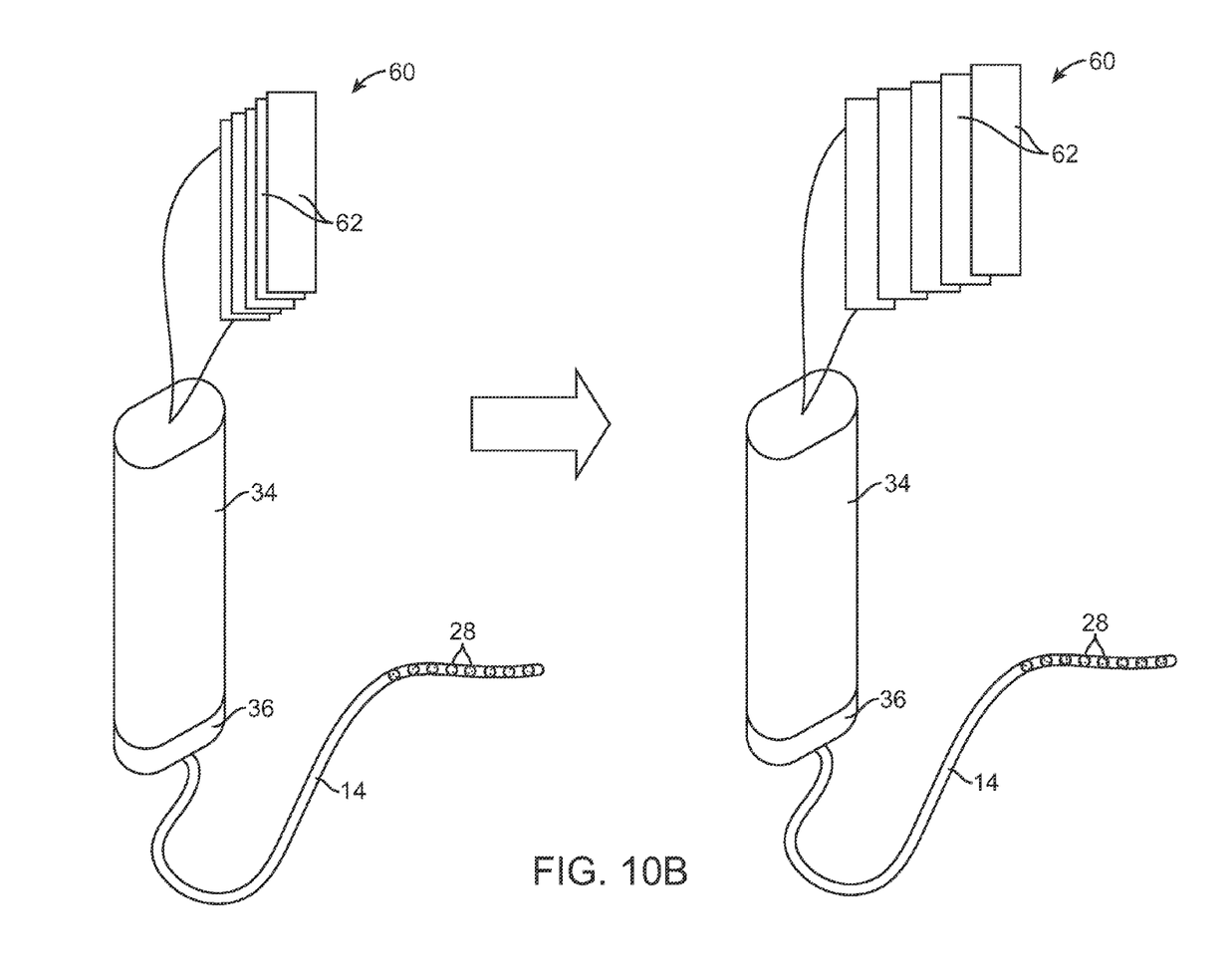

In another embodiment illustrated in FIG. 10B, an expandable electrode 60 is directly electrically coupled to the top of the case 34 via a conductor 62, and is therefore used to return electrical energy along with the case electrode(s). To allow for its expansion, the electrode 60 includes a plurality of stacked blades 62 much like the expandable electrode 56 described above, except that the stacked blades 62 are tied to each other at both ends. When the electrode 60 is in a non-expanded geometry, the stacked blades 62 are folded together (left side of FIG. 10B), so that it can be easily introduced into the patient's body during implantation. To place the electrode 60 is in an expanded geometry, the stacked blades 62 are laterally folded out, much like blinders (right side of FIG. 10B), thereby increasing the surface area of the electrode 60 after implantation. In the illustrated embodiment, the shape of the blades 62 is rectangular, although other shapes may be used, including those with rounded edges or triangular shapes.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy using a neurostimulator implanted within a tissue pocket of a patient, the neurostimulator having a case and a plurality of electrodes associated with the case, comprising:

conveying a single electrical pulse from the neurostimulator, thereby stimulating a target tissue site remote from the tissue pocket; and independently returning a plurality of electrical pulses respectively to the electrodes in a temporally interleaved fashion, wherein each electrical pulse returned to the respective electrodes has a shorter duration than the single electrical pulse.

2. The method of claim 1, wherein the electrodes form at least a portion of the case.

3. The method of claim 1, wherein the electrodes are discrete elements that are disposed on the case.

4. The method of claim 1, wherein the single electrical pulse is conveyed from the neurostimulator to at least one stimulation lead connected to the neurostimulator to stimulate the target tissue site.

5. The method of claim 1, wherein the single electrical pulse is independently returned to the electrodes to prevent inadvertent stimulation of the tissue pocket that would otherwise occur.

6. The method of claim 1, wherein multiple electrical pulses are returned to each of the electrodes while the single electrical pulse is conveyed from the neurostimulator.

7. The method of claim 1, wherein the plurality of electrodes comprises at least three electrodes, and the plurality of electrical pulses are serially returned to the at least three electrodes.

8. A neurostimulator, comprising:
a case;
a plurality of electrodes associated with the case;
one or more connectors configured for being coupled to one or more stimulation leads; and
stimulation circuitry contained within the case, the stimulation circuitry configured for conveying a single electrical pulse to the one or more stimulation leads, and independently returning the a plurality of electrical pulses respectively to the electrodes in a temporally interleaved fashion, wherein each electrical pulse returned to the respective electrodes has a shorter duration than the single electrical pulse.

9. The neurostimulator of claim 8, wherein the electrodes form at least a portion of the case.

10. The neurostimulator of claim 8, wherein the electrodes are segmented.

11. The neurostimulator of claim 8, wherein the stimulation circuitry is configured for returning multiple electrical pulses to each of the electrodes while conveying the single electrical pulse to the one or more stimulation leads.

12. The neurostimulator of claim 8, wherein the plurality of electrodes comprises at least three electrodes, and the stimulation circuitry is configured for serially returning the plurality of electrical pulses to the at least three electrodes.

13. The method of claim 1, further comprising:
conveying a plurality of electrical pulses from the neurostimulator, thereby stimulating the target tissue site remote from the tissue pocket; and
for each of the conveyed electrical pulses, independently returning the plurality of electrical pulses respectively to the electrodes, such that each electrical pulse returned to the respective electrodes has a shorter duration than the each conveyed electrical pulse.

14. The method of claim 1, wherein the plurality of electrical pulses are randomly returned to the electrodes.

15. The neurostimulator of claim 8, wherein the stimulation circuitry is configured for conveying of plurality of electrical pulses to the one or more stimulation leads, and, for each of the conveyed electrical pulses, independently returning the plurality of electrical pulses respectively to the electrodes, such that each electrical pulse returned to the respective electrodes has a shorter duration than the each conveyed electrical pulse.

16. The neurostimulator of claim 8, wherein the stimulation circuitry is configured for randomly returning the plurality of electrical pulses to the electrodes.

* * * * *